(12) United States Patent
Valsasina et al.

(10) Patent No.: US 8,927,530 B2
(45) Date of Patent: Jan. 6, 2015

(54) THERAPEUTIC COMBINATION COMPRISING A PLK1 INHIBITOR AND AN ANTINEOPLASTIC AGENT

(75) Inventors: Barbara Valsasina, Milan (IT); Italo Beria, Nerviano (IT); Antonella Ciavolella, Bizzarone (IT); Dario Ballinari, San Donato Milanese (IT); Enrico Pesenti, Parabiago (IT); Valter Domenico Croci, Nerviano (IT); Mara Emanuela Casnaghi, legal representative, Nerviano (IT); Alessandro Luciano Croci, legal representative, Nerviano (IT); Juergen Moll, Appiano Gentile (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 179 days.

(21) Appl. No.: 13/321,024

(22) PCT Filed: May 21, 2010

(86) PCT No.: PCT/EP2010/057027
§ 371 (c)(1),
(2), (4) Date: Jan. 19, 2012

(87) PCT Pub. No.: WO2010/136394
PCT Pub. Date: Dec. 2, 2010

(65) Prior Publication Data
US 2012/0114641 A1    May 10, 2012

(30) Foreign Application Priority Data

May 26, 2009 (EP) .................................. 09161111

(51) Int. Cl.
| | | |
|---|---|---|
| *A01N 43/54* | (2006.01) | |
| *C07D 239/42* | (2006.01) | |
| *C07D 401/04* | (2006.01) | |
| *C07D 471/22* | (2006.01) | |
| *C07D 487/04* | (2006.01) | |
| *A61K 31/515* | (2006.01) | |
| *A61K 45/06* | (2006.01) | |
| *A61K 31/282* | (2006.01) | |
| *A61K 31/337* | (2006.01) | |
| *A61K 31/4412* | (2006.01) | |
| *A61K 31/4745* | (2006.01) | |
| *A61K 31/4965* | (2006.01) | |
| *A61K 31/506* | (2006.01) | |
| *A61K 31/513* | (2006.01) | |
| *A61K 31/519* | (2006.01) | |
| *A61K 31/704* | (2006.01) | |
| *A61K 31/7068* | (2006.01) | |
| *A61K 33/24* | (2006.01) | |

(52) U.S. Cl.
CPC .............. *A61K 45/06* (2013.01); *A61K 31/282* (2013.01); *A61K 31/337* (2013.01); *A61K 31/4412* (2013.01); *A61K 31/4745* (2013.01); *A61K 31/4965* (2013.01); *A61K 31/506* (2013.01); *A61K 31/513* (2013.01); *A61K 31/519* (2013.01); *A61K 31/704* (2013.01); *A61K 31/7068* (2013.01); *A61K 33/24* (2013.01)
USPC ........ 514/183; 514/256; 514/257; 514/266.1; 514/266.2; 514/266.23; 514/266.4

(58) Field of Classification Search
USPC .......... 514/252.16, 252.17, 252.19, 256, 257, 514/266.1, 266.2, 266.23, 266.4
See application file for complete search history.

(56) References Cited

U.S. PATENT DOCUMENTS

| | | | | |
|---|---|---|---|---|
| 2003/0229112 | A1* | 12/2003 | Houghton ..................... | 514/283 |
| 2008/0107721 | A1* | 5/2008 | Lewis et al. .................... | 424/450 |
| 2010/0216808 | A1* | 8/2010 | Caruso et al. ............. | 514/252.17 |

FOREIGN PATENT DOCUMENTS

| | | | |
|---|---|---|---|
| WO | 2004/104007 A1 | 12/2004 | |
| WO | WO 2008/074788 | * | 6/2008 |
| WO | WO 2008074788 A1 | * | 6/2008 |

OTHER PUBLICATIONS

Farhat, F.S. et al. A General Review of the Role of Irinotecan (CPT11) in the Treatment of Gastric Cancer. Medical Oncology. vol. 24, pp. 37-146. Published 2007.*

(Continued)

*Primary Examiner* — Paul Zarek
*Assistant Examiner* — George W Kosturko
(74) *Attorney, Agent, or Firm* — Scully, Scott, Murphy & Presser, P.C.

(57) ABSTRACT

The present invention provides a combination comprising (a) a compound of formula (I) and (b) one or more antineoplastic agents selected from the group consisting of an antimetabolite agent, analkylating or alkylating-like agent, an intercalating agent, a topoisomerase I or II inhibitor, an antimitotic agent, a kinase inhibitor, a proteasome inhibitor and an antibody inhibiting a growth factor or its receptor, wherein active ingredients of the combination are present in each case in free form or in the form of a pharmaceutically acceptable salt or any hydrate or solvate thereof, useful in the treatment of tumors.

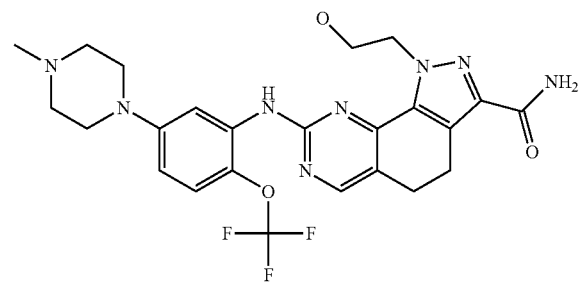

19 Claims, No Drawings

(56) References Cited

OTHER PUBLICATIONS

Farhat, F.S., et al. Medical Oncology. vol. 24, pp. 137-146, published 2007.*
Berenbaum, M.C., et al. J. Clin. Exp. Immunol. vol. 28, pp. 1-18. published 1977.*
Jackson J.R. et al., "Targeted Anti-Mitotic Therapies: Can We Improve on Tubulin Agents?", Nature Reviews Cancer 7(2):107-117 (Feb. 2007).

Warner S.L. et al., "Tubulin-Associated Drug Targets: Aurora Kinases, Polo-Like Kinases, and Others", Seminars in Oncology 33(4):436-448 (Aug. 2006).
International Search Report dated Nov. 15, 2010 received from the European Patent Office from related Application No. PCT/EP2010/057027.

* cited by examiner

THERAPEUTIC COMBINATION COMPRISING A PLK1 INHIBITOR AND AN ANTINEOPLASTIC AGENT

The present invention relates in general to the field of cancer treatment and, more particularly, provides an antitumor combination comprising a PLK1 inhibitor and one or more antineoplastic agents, endowed with a good antineoplastic effect.

Cancers are a leading cause of death in humans; surgery, radiation and chemotherapy are the useful means to fight cancers. In particular, combined chemotherapy, designed to treat cancer by using more than one drug in combination or association, is a well-accepted modality of treatment of neoplastic diseases such as cancer. Several efforts have been and are still being undertaken in order to select antitumor combinations more and more active and safe to be administered to a patient suffering from a cancer. The increase of the antitumor efficacy of a known antitumor compound by administering the same in combination with one or more different antitumor drugs in order to reduce the toxic effects of the individual agents when used alone, and in some instances because the combination has greater efficacy than when either agent is used alone, is a strongly felt need in the field of anticancer therapy. Expression of PLK1 is seen in all proliferating normal tissues while overexpression is observed in a series of tumors including breast, prostate, ovary, lung, gastric and colon cancers. Upon PLK1 depletion in cancer cell by RNAi, inhibition of proliferation and decreased viability resulting in cell-cycle arrest with 4 N DNA content followed by apoptosis is observed. Although four different PLKs family members are described in humans, the inhibition of the enzymatic activity or the depletion of PLK1 is sufficient to induce G2/M cell cycle block and apoptosis in tumor cell lines and tumor regression in xenograft models. In addition, for the other PLKs, a tumor suppressor function has been described and PLK2 and PLK3—but not PLK1—are reported to be expressed in non-proliferating, differentiated post mitotic cells, like neurons, indicating a possible better safety profile for a PLK1 specific compound (see for instance: Strebhardt K, et al., Nat Rev Cancer 2006; 6(4):321-30)

The use of mitotic inhibitors in cancer therapy is a widely accepted clinical strategy for the treatment of a broad range of human cancers (see for instance: Jackson J R, et al., Nature Reviews Cancer 2007; 7, 107-117). Taxanes (paclitaxel and docetaxel) and vinca alkaloids (vincristine and vinblastine) work by either stabilizing or destabilizing microtubules with catastrophic consequences in cells progressing through mitosis. They are first line therapeutics for several tumor types including Hodgkin's disease, non-Hodgkin's lymphoma, testicular cancer, neuroblastoma and Wilms' tumor (vinca alkaloids) and second line in cisplatin-refractory ovarian, breast, lung and esophagus cancers (Taxanes). However, due to the role of microtubules in processes such as cell migration, phagocytosis and axonal transport certain toxicities such as peripheral neuropathy are frequently observed with these agents.

Pyrazoloquinazolines described and claimed in the patent application WO2008074788 (Nerviano Medical Sciences Srl.) are potent inhibitors of PLK1 and are thus useful in the treatment of proliferative disorders, especially cancer. The compound of formula (I) is one of the compounds described and claimed in the above noted patent application. Also its preparation, pharmaceutical compositions comprising it and medical uses are described and claimed there. It has now been surprisingly found that the antitumor effect of the compound of formula (I) is greatly enhanced when it is administered in combination with known antineoplastic agents.

The present invention provides new combinations comprising (a) a compound of formula (I) and (b) one or more known antineoplastic agents. These combinations are particularly suitable for the treatment of proliferative disorders, especially cancer.

More specifically, the combinations of the present invention are very useful in therapy as antitumor agents and lack, in terms of both toxicity and side effects, the drawbacks associated with currently available antitumor drugs. It is therefore an object of the present invention a combination comprising (a) a compound of formula (I)

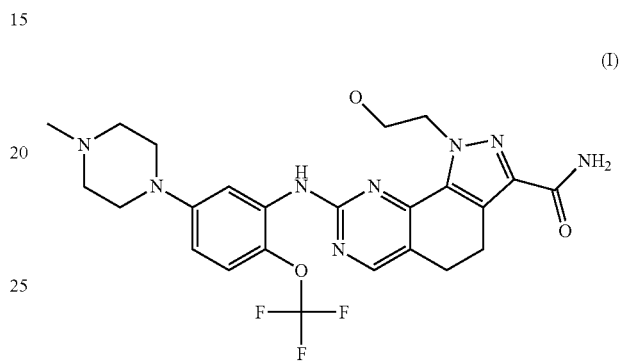

and (b) one or more antineoplastic agents selected from the group consisting of an antimetabolite agent, an alkylating or an alkylating-like agent, an intercalating agent, a topoisomerase I or II inhibitor, an antimitotic agent, a kinase inhibitor, a proteasome inhibitor and an antibody inhibiting a growth factor or its receptor, wherein the active ingredients of the combination are present in each case in free form or in the form of a pharmaceutically acceptable salt or any hydrate or solvate thereof.

Another aspect relates to a combination according to the invention for simultaneous, separate or sequential use. Another aspect relates to a combination according to the invention for use in treating or delaying the progression of a proliferative disorder.

A further aspect of the invention relates to the use of a combination according to the invention in the preparation of a medicament for treating or delaying the progression of a proliferative disorder, wherein the said use comprises the simultaneous, sequential or separate administration to a subject in need thereof of the therapeutic combination. Moreover, the invention relates to a pharmaceutical composition comprising a combination according to the invention admixed with a pharmaceutically acceptable carrier, diluent or excipient.

Another aspect relates to a pharmaceutical composition according to the invention for use in treating or delaying the progression of a proliferative disorder.

A further aspect of the invention relates to the use of a pharmaceutical composition according to the invention in the preparation of a medicament for treating or delaying the progression of a proliferative disorder, wherein the said use comprises the simultaneous, sequential or separate administration to a subject in need thereof of the pharmaceutical composition.

Furthermore, the invention relates to a method of treating a proliferative disorder, said method comprising simultaneously, sequentially or separately administering a combination of the invention to a subject in need thereof. Another aspect relates to a method of treating a proliferative disorder, said method comprising simultaneously, sequentially or separately administering a pharmaceutical composition of the invention to a subject in need thereof. Another aspect relates to a method for lowering the side effects caused by antineoplastic therapy with an antineoplastic agent in mammals, including humans, in need thereof, said method comprising administering to said mammal a combined preparation comprising (a) a compound of formula (I) as defined in claim 1 and (b) one or more antineoplastic agents selected from the group consisting of an antimetabolite agent, an alkylating or alkylating-like agent, an intercalating agent, a topoisomerase I or II inhibitor, an antimitotic agent, a kinase inhibitor, a proteasome inhibitor and an antibody inhibiting a growth factor or its receptor, in amounts effective to produce a synergic antineoplastic effect.

The present invention further provides a commercial kit comprising, in a suitable container means, (a) a compound of formula (I) as defined above, and (b) one or more antineoplastic agents selected from the group consisting of an antimetabolite agent, an alkylating or alkylating-like agent, an intercalating agent, a topoisomerase I or II inhibitor, an antimitotic agent, a kinase inhibitor, a proteasome inhibitor and an antibody inhibiting a growth factor or its receptor. In a kit according to the invention, (a) a compound of formula (I), as defined above, and (b) one or more antineoplastic agents selected from the group consisting of an antimetabolite agent, an alkylating or alkylating-like agent, an intercalating agent, a topoisomerase I or II inhibitor, an antimitotic agent, a kinase inhibitor, a proteasome inhibitor and an antibody inhibiting a growth factor or its receptor, are present within a single container means or within distinct container means.

Another embodiment of the present invention is a commercial kit comprising a pharmaceutical composition as described above.

Kits according to the invention are intended for simultaneous, separate or sequential use in antitumor therapy. Kits according to the invention are intended for use in anticancer therapy.

According to a preferred embodiment of the invention, the combination of the present invention comprises a compound of formula (I) and an antimetabolite agent selected from the group consisting of 5-fluorouracil, azacytidine, capecitabine, cytarabine, gemcitabine, pemetrexed, methotrexate, edatrexate, hydroxyurea, fludarabine and mercaptopurine.

Preferably, the antimetabolite agent to be used in the present invention is gemcitabine or cytarabine.

According to another preferred embodiment of the invention, the combination of the present invention comprises a compound of formula (I) and an alkylating or alkylating-like agent selected from the group consisting of nitrogen mustards (mechlorethamine, cyclophosphamide, ifosfamide, melphalan and chlorambucil), aziridines (thiotepa), nitrosoureas (carmustine, lomustine, semustine), triazenes (dacarbazine and temozolomide) and platinum derivatives (cisplatin, oxaliplatin, carboplatin and satraplatin).

More preferably, the alkylating or alkylating-like agent to be used in the present invention is cisplatin.

According to another preferred embodiment of the invention the combination of the present invention comprises a compound of formula (I) and an intercalating agent; preferably the intercalating agent is bleomycin.

According to another preferred embodiment of the invention the combination of the present invention comprises a compound of formula (I) and a topoisomerase I inhibitor selected from the group consisting of topotecan, SN-38, CPT11 and 9-nitrocamptothecin.

More preferably, the topoisomerase I inhibitor is SN-38 or CPT11.

According to another preferred embodiment of the invention, the combination of the present invention comprises a compound of formula (I) and a topoisomerase II inhibitor selected from the group consisting of doxorubicin, epirubicin, idarubicin, nemorubicin, mitoxantrone, etoposide and teniposide.

Preferably, the topoisomerase II inhibitor is doxorubicin.

According to another preferred embodiment of the invention, the combination of the present invention comprises a compound of formula (I) and an antimitotic agent selected from the group consisting of paclitaxel, docetaxel, ixabepilone, vinblastine, vincristine, vindesine and vinorelbine.

More preferably, the antimitotic agent is paclitaxel.

According to another preferred embodiment of the invention, the combination of the present invention comprises a compound of formula (I) and a kinase inhibitor selected from the group consisting of sorafenib, dasatinib, gefitinib, erlotinib, sunitinib, imatinib, nilotinib and lapatinib.

According to another preferred embodiment, the kinase inhibitor is sorafenib or dasatinib.

According to another preferred embodiment of the invention, the combination of the present invention comprises a compound of formula (I) and a proteasome inhibitor; preferably, the proteasome inhibitor is bortezomib.

According to another preferred embodiment of the invention, the combination of the present invention comprises a compound of formula (I) and an antibody inhibiting a growth factor or its receptor selected from the group consisting of bevacizumab (antibody to vascular endothelial growth factor), cetuximab, panitumumab, matuzumab, nimotuzumab (antibodies to epidermal growth factor receptor), trastuzumab and pertuzumab (antibodies to ErbB2).

According to another preferred embodiment, the antibody is bevacizumab.

By the term "a synergic antineoplastic effect" as used herein is meant the inhibition of the growth tumor, preferably the complete regression of the tumor, by administering an effective amount of the combination of the compound of formula (I) as defined above and one or more antineoplastic agents selected from the group consisting of an antimetabolite agent, an alkylating or alkylating-like agent, an intercalating agent, a topoisomerase I or II inhibitor, an antimitotic agent, a kinase inhibitor, a proteasome inhibitor and an antibody inhibiting a growth factor or its receptor to mammals, including human.

The term "combined preparation" as used herein defines especially a "kit of parts" in the sense that the combination partners (a) and (b) as defined above can be dosed independently or by use of different fixed combinations with distinguished amounts of the combination partners (a) and (b), i.e. simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutic effect in a non-effective dosage of one or both of the combination partners (a) and (b), and very preferably a strong synergism of the combination partners (a) and (b).

By the term "administered" or "administering" as used herein is meant parenteral and/or oral administration. By "parenteral" is meant intravenous, subcutaneous and intramuscolar administration.

For the administration of the compound of formula (I) the course of therapy generally employed is from about 5 to about 500 mg per dose, from 1 to 5 times daily.

The compound of formula (I) can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion. In the method of the subject invention, for the administration of an antimetabolite agent, preferably cytarabine or gemcitabine, the course of therapy generally employed is from 200 mg/m$^2$ to 5000 mg/m$^2$ of body surface area as weekly administration. More preferably, the course of therapy generally employed is from about 500 mg/m$^2$ to 1250 mg/m$^2$ on days 1 and 8 of a 21-day cycle or on days 1, 8 and 15 of a 28-day cycle or on day 1 of a 21-day cycle. For the administration of an alkylating agent, preferably temozolomide, the course of therapy generally employed is from 15 mg/m$^2$ to 300 mg/m$^2$ of body surface area daily. More preferably, the course of therapy generally employed is from about 50 mg/m$^2$ to 150 mg/m$^2$ daily for up to 42 consecutive days.

For the administration of a platinum derivative, preferably cisplatin, the course of therapy generally employed is from 10 mg/m$^2$ to 100 mg/m$^2$ of body surface area daily every 2-3 weeks. More preferably, the course of therapy generally employed is from about 30 mg/m$^2$ to 85 mg/m$^2$ on day 1, once every 2 weeks. For the administration of an intercalating agent, preferably bleomycin, the course of therapy generally employed is from 1 U/m2 to 100 U/m2 of body surface area weekly or twice weekly.

For the administration of a topoisomerase I inhibitor, preferably CPT-11, the course of therapy generally employed is from 1 mg/m$^2$ to 500mg/m$^2$ of body surface area daily for 2-10 consecutive days. More preferably, the course of therapy generally employed is from about 50 mg/m$^2$ to 350 mg/m$^2$ weekly or every two weeks or every three weeks. For the administration of a topoisomerase II inhibitor, preferably doxorubicin, the course of therapy generally employed is from 0.1 mg/m$^2$ to 500 mg/m$^2$ of body surface area daily for 2-10 consecutive days. More preferably, the course of therapy generally employed is from about 0.5 mg/m$^2$ to 100 mg/m$^2$ daily for 3-5 consecutive days in a 21-day cycle.

For the administration of an antimitotic agent, preferably paclitaxel, the course of therapy generally employed is from about 50 mg/m$^2$ to 100 mg/m$^2$ of body surface area every three weeks or from 30 mg/m$^2$ weekly.

For the administration of a kinase inhibitor, preferably sorafenib, the course of therapy generally employed may be from 1 mg to 5000 mg. More preferably, the course of therapy employed is from about 10 mg to 2000 mg.

For the administration of a proteasome inhibitor, preferably bortezomib, the course of therapy generally employed is from 0.1 mg/m$^2$ to 30 mg/m$^2$ of body surface area every three weeks.

Finally, for the administration of an antibody inhibiting a growth factor or its receptors, preferably bevacizumab, the course of therapy generally employed may be from 0.1 mg/kg to 100 mg/kg. More preferably the course of therapy employed is from 1 mg/kg to 20 mg/kg on day 1 of a three weeks cycle.

When the active constituents of the combined preparation according to the invention are supplied along with a pharmaceutically acceptable carrier or excipient, a pharmaceutical composition is formed. Such pharmaceutical composition constitutes a further embodiment of the invention.

Pharmaceutically acceptable carriers and excipients are chosen such that side effects from the pharmaceutical compound are minimized and the performance of the compound is not cancelled or inhibited to such an extent that treatment is ineffective.

Pharmaceutically acceptable carriers or excipients to be utilized in the preparation of a pharmaceutical composition according to the invention are well known to people skilled in the art of formulating compounds in a form of pharmaceutical compositions. For example, "pharmaceutically acceptable carrier" refers to one or more compatible solid or liquid filler, diluent or encapsulating substances which are suitable for administration to mammals including humans. For example, "pharmaceutically acceptable excipient" refers to any inert substance used as a diluent or vehicle for an active substance(s) that is intentionally added to the formulation of a dosage form. The term includes binders, fillers' disintegrants, and lubricants.

Nevertheless, the combination of the present invention can be employed without adding any sustained-release adjuvant.

Techniques for formulation and administration of drugs can be found in "Remington's Pharmacological Sciences"; Mack Publishing Co., Easton, Pa., latest edition.

Pharmaceutical compositions suitable for parenteral administration are formulated in a sterile form. The sterile composition thus may be a sterile solution or suspension in a non-toxic parenterally acceptable diluent or solvent. The amount of an active ingredient contained in the pharmaceutical composition according to the invention may vary quite widely depending upon many factors such as, for example, the administration route and the vehicle. The combinations and the pharmaceutical compositions according to the invention are useful in anticancer therapy. The antineoplastic therapy of the present invention is in particular suitable for treating all form of cancer including, but not limited to: carcinoma such as bladder, breast, colon, kidney, liver, lung, including small cell lung cancer, oesophagus, gall-bladder, ovary, pancreas, stomach, cervix, thyroid, prostate, and skin, including squamous cell carcinoma; haematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; haematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; mesothelioma; tumors of the central and peripheral nervous system, including astrocytoma neuroblastoma, glioma and schwannomas; other tumors, including mesothelioma, melanoma, seminoma, teratocarcinoma, osteosarcoma, xeroderma pigmentosum, keratoxanthoma, thyroid follicular cancer and Kaposi's sarcoma.

Due to the key role of PLK1 in the regulation of cellular proliferation, the combinations and the pharmaceutical compositions of the present invention are also useful in the treatment of a variety of cell proliferative disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

The combinations and the pharmaceutical compositions of this invention, as modulators of apoptosis, may also be useful in the treatment of cancer, viral infections, prevention of AIDS development in HIV-infected individuals, autoimmune diseases and neurodegenerative disorders.

The antineoplastic effect of the combined preparations of the present invention is shown, for instance, by the following in vitro tests, which are intended to illustrate the present invention without posing any limitation to it.

EXAMPLES

Materials and Methods

Exponentially growing human pancreatic carcinoma (MiaPaCa, Capan-1), human colon carcinoma (HCT-116), leukemia (HL60) and multiple myeloma (KMS11) cell lines were seeded and incubated at 37° C. in a humidified 5% CO2 atmosphere. Drugs were added to the experimental culture, and incubations were carried out at 37° C. for 72 hours in the dark. The MCF7 breast cancer cell line was seeded and incubated at 37° C. in a humidified 5% CO2 atmosphere. Drugs were added to the experimental culture, and incubations were carried out at 37° C. for 120 hours in the dark. Scalar doses of the compound of formula (I) and antineoplastic agents were added to the medium 24 hours after seeding. Two treatment schedules were tested: simultaneous administration (both drugs administered to cells for 72/120 hours) and sequential administration (the compound of formula (I) administered 24 hours after other agents). Drug solutions were prepared immediately before use. At the end of treatment, cell proliferation was determined by a intracellular adenosine triphosphate monitoring system (CellTiterGlo-Promega) using an Envision (PerkinElmer) reader. Inhibitory activity was evaluated comparing treated versus control data using the Assay Explorer (MDL) program. The dose inhibiting 50% of cell growth was calculated using sigmoidal interpolation curve. Combination indices (C.I.) were calculated using a proprietary computer program for multiple drug effect analysis based on the equation of Chou-Talalay (Adv Enzyme Regul 1984;22:27-55) for mutually nonexclusive drugs, where a C.I. of <1 indicates a more than additive effect: C.I.: >3 strong antagonism; 1.3-3 antagonism; 1.2-0.8 additivity; 0.8-0.3 synergism; <0.3 strong synergism.

Example 1

In Vitro Cytotoxic Activity of the Combination of the Compound of Formula (I) with Gemcitabine In table 1 the results showing synergism of the compound of formula (I) with gembitabine (i.e. 0.3<C.I.<0.8) are reported for the Capan-1 human pancreatic carcinoma cell line.

TABLE 1

| Cell line | Drug | | | Combination Index |
|---|---|---|---|---|
| | Compound of formula (I) μM | Gemcitabine μM | Schedule | |
| Capan-1 human pancreatic carcinoma | 10 | 5 | Simultaneous | 0.51 |
| | 10 | 10 | | 0.57 |
| | 5 | 10 | | 0.76 |
| | 2.5 | 10 | | 0.77 |

Example 2

In Vitro Cytotoxic Activity of the Combination of the Compound of Formula (I) with Cisplatin In table 2 the results showing synergism of the compound of formula (I) with cisplatin (i.e. 0.3<C.I.<0.8) are reported for the HCT-116 human colon carcinoma cell line.

TABLE 2

| Cell line | Drug | | | Combination Index |
|---|---|---|---|---|
| | Compound of formula (I) μM | Cisplatin μM | Schedule | |
| HCT-116 human colon carcinoma | 0.2 | 25 | Sequential | 0.61 |
| | 0.2 | 50 | | 0.46 |
| | 0.1 | 50 | | 0.41 |
| | 0.05 | 50 | | 0.72 |

Example 3

In Vitro Cytotoxic Activity of the Combination of a Compound of Formula (I) with SN-38

In table 3 the results showing synergism of the compound of formula (I) with SN-38 (i.e. 0.3<C.I.<0.8) are reported for the HCT-116 human colon carcinoma cell line.

TABLE 3

| Cell line | Drug | | | Combination Index |
|---|---|---|---|---|
| | Compound of formula (I) μM | SN-38 μM | Schedule | |
| HCT-116 human colon carcinoma | 0.1 | 0.05 | Simultaneous | 0.70 |
| | 0.1 | 0.1 | | 0.53 |
| | 0.05 | 0.1 | | 0.56 |
| | 0.025 | 0.1 | | 0.49 |

Example 4

In Vitro Cytotoxic Activity of the Combination of a Compound of Formula (I) with Doxorubicin In table 4 the results showing synergism of the compound of formula (I) with doxorubicin (i.e. 0.3<C.I.<0.8) are reported for the HL-60 human leukemia cell line.

TABLE 4

| Cell line | Drug | | | Combination Index |
|---|---|---|---|---|
| | Compound of formula (I) μM | Doxorubicin μM | Schedule | |
| HL-60 Human leukemia | 0.1 | 0.5 | Simultaneous | 0.51 |
| | 0.1 | 1 | | 0.36 |
| | 0.05 | 1 | | 0.57 |
| | 0.025 | 1 | | 0.51 |

Example 5

In Vitro Cytotoxic Activity of the Combination of a Compound of Formula (I) with Paclitaxel In table 5 the results showing synergism of the compound of formula (I) with taxol (i.e. 0.3<C.I.<0.8) are reported for HCT-116 human colon carcinoma, HL60 human leukemia and KMS11 human multiple myeloma cell lines.

TABLE 5

| Cell line | Drug | | Schedule | Combination Index |
|---|---|---|---|---|
| | Compound of formula (I) μM | Paclitaxel μM | | |
| HCT-116 human colon carcinoma | 0.1 | 0.1 | Simultaneous | 0.54 |
| | 0.05 | 0.1 | | 0.42 |
| | 0.025 | 0.1 | | 0.39 |
| HCT-116 human colon carcinoma | 0.2 | 0.1 | Sequential | 0.42 |
| | 0.1 | 0.1 | | 0.45 |
| | 0.05 | 0.1 | | 0.44 |
| HL-60 human leukemia | 0.1 | 0.1 | Simultaneous | 0.68 |
| | 0.05 | 0.1 | | 0.52 |
| | 0.025 | 0.1 | | 0.54 |
| HL-60 human leukemia | 0.2 | 0.1 | Sequential | 0.54 |
| | 0.1 | 0.1 | | 0.45 |
| | 0.05 | 0.1 | | 0.46 |
| KMS-11 human multiple myeloma | 0.1 | 0.05 | Simultaneous | 0.65 |
| | 0.1 | 0.1 | | 0.39 |
| | 0.05 | 0.1 | | 0.40 |
| | 0.025 | 0.1 | | 0.34 |
| KMS-11 human multiple myeloma | 0.2 | 0.1 | Sequential | 0.59 |
| | 0.1 | 0.1 | | 0.59 |
| | 0.05 | 0.1 | | 0.54 |

Example 6

In Vitro Cytotoxic Activity of the Combination of a Compound of Formula (I) with Sorafenib In table 6 the results showing synergism of the compound of formula (I) with sorafenib (i.e. 0.3<C.I.<0.8) are reported for HCT-116 human colon carcinoma and Mia-PaCa human pancreatic carcinoma cell lines.

TABLE 6

| Cell line | Drug | | Schedule | Combination Index |
|---|---|---|---|---|
| | Compound of formula (I) μM | Sorafenib μM | | |
| HCT-116 human colon carcinoma | 0.2 | 5 | Sequential | 0.55 |
| | 0.2 | 10 | | 0.65 |
| | 0.1 | 10 | | 0.58 |
| | 0.05 | 10 | | 0.58 |
| Mia-PaCa human pancreatic carcinoma | 0.2 | 5 | Sequential | 0.65 |
| | 0.2 | 10 | | 0.57 |
| | 0.1 | 10 | | 0.54 |
| | 0.05 | 10 | | 0.64 |

Example 7

In Vitro Cytotoxic Activity of the Combination of a Compound of Formula (I) with Dasatinib In table 7 the results showing synergism of the compound of formula (I) with dasatinib (i.e. 0.3<C.I.<0.8) are reported for the MCF7 breast cancer cell line after 120 hours treatment.

TABLE 7

| Cell line | Drug | | Schedule | Combination Index |
|---|---|---|---|---|
| | Compound of formula (I) μM | dasatinib μM | | |
| MCF7 human breast carcinoma | 10 | 5 | Simultaneous | 0.45 |
| | 10 | 10 | | 0.48 |
| | 5 | 10 | | 0.52 |
| | 2.5 | 10 | | 0.47 |

Example 8

In Vitro Cytotoxic Activity of the Combination of a Compound of Formula (I) with Bortezomib In table 8 the results showing synergism of the compound of formula (I) with bortezomib (i.e. 0.3<C.I.<0.8) are reported for KMS11 human multiple myeloma and Mia-PaCa human pancreatic carcinoma cell lines.

TABLE 8

| Cell line | Drug | | Schedule | Combination Index |
|---|---|---|---|---|
| | Compound of formula (I) μM | Bortezomib μM | | |
| KMS-11 human multiple myeloma | 0.05 | 0.1 | Simultaneous | 0.57 |
| Mia-PaCa human pancreatic carcinoma | 0.025 | 0.1 | Simultaneous | 0.61 |

Example 9

In Vitro Cytotoxic Activity of the Combination of the Compound of Formula (I) with Cytarabine In table 9 the results showing synergism of the compound of formula (I) with cytarabine (i.e. 0.3<C.I.<0.8) are reported for the HL-60 human promyelocytic leukemia cell line.

TABLE 9

| Cell line | Drug | | Schedule | Combination Index |
|---|---|---|---|---|
| | NMS-1286937 μM | Cytarabine μM | | |
| HL60 leukemia | 0.1 | 5 | Sequential | 0.59 |
| | 10 | 0.05 | | 0.47 |
| | 10 | 0.025 | | 0.58 |
| | 2.5 | 10 | | 0.67 |

Example 10

In Vivo Cytotoxic Activity of the Combination of a Compound of Formula (I) with CPT11

Balb, Nu/Nu male mice, from Harlan (Italy), were maintained, in agreement with the European Communities Council Directive no. 86/609/EEC, in cages with paper filter cover, food and bedding sterilized and acidified water.

Fragments of HT29 human colon cancer tumors were implanted subcutaneously. The treatment started when tumors were palpable. Compound of formula (I) was administered by oral route at the doses of 45 and 60 mg/kg daily on day 2, 3, 4, 6, 7 and 8. CPT11 was administered by intravenous route at the dose of 45 mg/kg on days 1, 5, 9. When combined, compound of formula (I) was administered on day 2, 3, 4, 6, 7 and 8, and CPT11 on days 1, 5, 9. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Sinergy was identified when T-C of drug combination is >of addition of T-C value of single agents.

Toxicity was evaluated on the basis of body weigh reduction. The results are reported in table 10.

TABLE 10

| Treatment | T-C (days) | Toxicity |
|---|---|---|
| Compound of formula (I) 45 mg/kg* | 10.3 | 0/7 |
| CPT11 45 mg/kg** | 12.3 | 0/7 |
| CPT11 45 mg/kg + Compound of formula (I) 45 mg/kg*** | 36 | 0/7 |

*Oral treatments made on day 2, 3, 4, 6, 7, 8
**Treatments made by intravenous route at days 1, 5, 9
***Compound of formula (I) treatments days 2, 3, 4, 6, 7, 8; CPT11 treatments days 1, 5, 9

The compound of formula (I) combined with CPT 11 produced a clear synergic effect. The T-C observed when compound of formula (I) was combined with CPT11 was superior to the expected by the simple addition of T-C obtained by the single treatments. No toxicity was observed in any of the treatment group.

Example 11

In Vivo Cytotoxic Activity of the Combination of a Compound of Formula (I) with 5FU Balb, Nu/Nu male mice, from Harlan (Italy), were maintained, in agreement with the European Communities Council Directive no. 86/609/EEC, in cages with paper filter cover, food and bedding sterilized and acidified water. Fragments of HT29 human colon cancer tumors were implanted subcutaneously. The treatment started when tumors were palpable. Compound of formula (I) was administered by oral route at the doses of 45 mg/kg daily on day 2, 3, 4, 6, 7 and 8, 5FU was administered by intravenous route at the dose of 50 mg/kg on days 1, 5 and 9. When combined, compound of formula (I) was administered on day 2, 3, 4, 6, 7 and 8, and 5-FU on days 1, 5 and 9. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Sinergy was identified when T-C of drug combination is >of addition of T-C value of single agents, additivity is identified when T-C value of drug combination is equal to addition of T-C value of single agents.

Toxicity was evaluated on the basis of body weigh reduction. The results are reported in table 11.

TABLE 11

| Treatment | T-C (days) | Toxicity |
|---|---|---|
| Compound of formula (I) 45 mg/kg* | 10.3 | 0/7 |
| 5FU 50 mg/kg** | 11.4 | 0/7 |
| 5FU 50 mg/kg + Compound of formula (I) 45 mg/kg*** | 21.27 | 0/7 |

*Oral treatments made on day 2, 3, 4, 6, 7, 8
**Treatments made by intravenous route at days 1, 5, 9
***Compound of formula (I) treatments days 2, 3, 4, 6, 7, 8; 5FU treatments days 1, 5, 9

The T-C observed when compound of formula (I) was combined with 5FU is similar to the expected by the simple addition of T-C obtained by the single treatments indicating additivity.

Example 12

In Vivo Cytotoxic Activity of the Combination of a Compound of Formula (I) with Bevacizumab Balb, Nu/Nu male mice, from Harlan (Italy), were maintained, in agreement with the European Communities Council Directive no. 86/609/EEC, in cages with paper filter cover, food and bedding sterilized and acidified water.

Fragments of HT29 human colon cancer tumors were implanted subcutaneously. The treatment started when tumors were palpable. Compound of formula (I) was administered by oral route in a volume of 10 ml/kg at the doses of 45 and 60 mg/kg daily on day 2, 3, 4, 6, 7, 8, 10, 11 and 12. Bevacizumab was administered by intraperitoneal route at the dose of 20 mg/kg on days 1, 5, 9 and 13. When combined, compound of formula (I) was administered on day 2, 3, 4, 6, 7, 8, 10, 11 and 12 and bevacizumab on days on days 1, 5, 9 and 13. Tumor growth and body weight were measured every 3 days. Tumor growth was assessed by caliper. The two diameters were recorded and the tumor weight was calculated according the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Sinergy was identified when T-C of drug combination is >of addition of T-C value of single agents, additivity is identified when T-C value of drug combination is equal to addition of T-C value of single agents. Toxicity was evaluated on the basis of body weigh reduction. The results are reported in table 12.

TABLE 12

| Treatment | T-C (days) | Toxicity |
|---|---|---|
| Compound of formula (I) 45 mg/kg* | 8.5 | 0/7 |
| Compound of formula (I) 60 mg/kg* | 16.8 | 0/7 |
| Bevacizumab 20 mg/kg** | 4.7 | 0/7 |
| Bevacizumab 20 mg/kg + Compound of formula (I) 45 mg/kg*** | 13.7 | 0/7 |
| Bevacizumab 20 mg/kg + Compound of formula (I) 60 mg/kg*** | 19.4 | 0/7 |

*Oral treatments made on day 2, 3, 4, 6, 7, 8, 10, 11, 12.
**Treatments made by intravenous route at days 1, 5, 9, 13.
***Compound of formula (I) treatments days 2, 3, 4, 6, 7, 8, 10, 11, 12 bevacizumab treatments, days 1, 5, 9, 13.

The T-C observed when compound of formula (I) was combined with bevacizumab was similar to the expected by the simple addition of T-C obtained by the single treatments. No toxicity was observed in any of the treatment group.

Example 13

In Vivo Cytotoxic Activity of the Combination of a Compound of Formula (I) with Cytarabine SCID female mice, from Harlan (Italy), were maintained, in agreement with the European Communities Council Directive no. 86/609/EEC, in cages with paper filter cover, food and bedding sterilized and acidified water. $5 \times 10^6$ in 0.2 ml AML-PS acute myeloid leukaemia cells were injected intravenously in mice.

Compound of formula (I) was administered by oral route at the dose of 120 mg/kg on days 2, 3, 14, 15, 26, 27, 38, 39. Cytarabine was administered by intraperitoneal route at the dose of 75 mg/kg on days 2, 3, 4, 5, 6, 14, 15, 16, 17, 18, 26, 27, 28, 29, 30, 38, 39, 40, 41 42. When combined, compound of formula (I) was administered on days 2, 3, 14, 15, 26, 27, 38, 39 and cytarabine on days 2, 3, 4, 5, 6, 14, 15, 16, 17, 18, 26, 27, 28, 29, 30, 38, 39, 40, 41 42. Body weight was measured every 3 days. The effect of the antitumor treatment was evaluated determining the Median Survival Time of treated animals respect to control group. Results are reported in table 13.

The antitumor efficacy in the combination group is statistically significant respect to the single treatments groups, indicating a potential synergysm of a combined treatment with Compound of formula (I) and Cytarabine. No toxicity was observed.

TABLE 13

| Treatment | Median Survival Time | Toxicity |
| --- | --- | --- |
| Control | 34 | 0/7 |
| Compound of formula (I) 120 mg/kg* | 49.5 | 0/7 |
| cyarabine 75 mg/kg** | 66.5 | 0/7 |
| Cytarabine 75 mg/kg + Compound of formula (I) 120 mg/kg*** | 78.5 | 0/7 |

*Oral treatments made on day 2, 3, 14, 15, 26, 27, 38, 39,
**Treatments made by intraperitoneal route at days days 2, 3, 4, 5, 6, 14, 15, 16, 17, 18, 26, 27, 28, 29, 30, 38, 39, 40, 41 42
***Compound of formula (I) oral treatments days 2, 3, 14, 15, 26, 27, 38, 39, cytarabine treatments, intraperitoneal route at days 2, 3, 4, 5, 6, 14, 15, 16, 17, 18, 26, 27, 28, 29, 30, 38, 39, 40, 41 42,

The invention claimed is:

1. A combination comprising a synergistic amount of (a) a compound of formula (I)

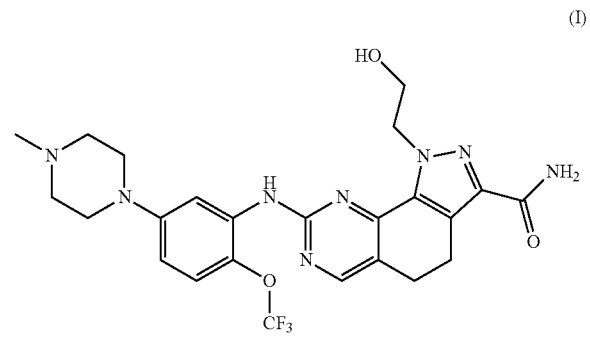 [SMILES: CN1CCN(c2ccc(OC(F)(F)F)c(Nc3ncc4c(n3)-c3c(c(C(N)=O)nn3CCO)CC4)c2)CC1]

(I)

and (b) one or more antineoplastic agents selected from the group consisting of an antimetabolite agent, an alkylating or an alkylating-like agent, an intercalating agent, a topoisomerase I or II inhibitor, an antimitotic agent, a kinase inhibitor, a proteasome inhibitor and an antibody inhibiting a growth factor or its receptor, wherein the active ingredients of the combination are present in each case in free form or in the form of a pharmaceutically acceptable salt or any hydrate or solvate thereof, wherein the topoisomerase I inhibitor is selected from the group consisting of topotecan, SN-38, CPT11 and 9-nitrocamptothecin.

2. The combination according to claim 1 wherein the antimetabolite agent is selected from the group consisting of 5-fluorouracil, azacytidine, capecitabine, cytarabine, gemcitabine, pemetrexed, methotrexate, edatrexate, hydroxyurea, fludarabine and mercaptopurine.

3. The combination according to claim 2 wherein the antimetabolite agent is gemcitabine or cytarabine.

4. The combination according to claim 1 wherein the alkylating or alkylating-like agent is selected from the group consisting of nitrogen mustards (mechlorethamine, cyclophosphamide, ifosfamide, melphalan and chlorambucil), aziridines (thiotepa), nitrosoureas (carmustine, lomustine, semustine), triazenes (dacarbazine and temozolomide) and platinum derivatives (cisplatin, oxaliplatin, carboplatin and satraplatin).

5. The combination according to claim 4 wherein the alkylating or alkylating-like agent is cisplatin.

6. The combination according to claim 1 wherein the intercalating agent is bleomycin.

7. The combination according to claim 1 wherein the topoisomerase I inhibitor is SN-38 or CPT11.

8. The combination according to claim 1 wherein the topoisomerase II inhibitor is selected from the group consisting of doxorubicin, epirubicin, idarubicin, nemorubicin, mitoxantrone, etoposide and teniposide.

9. The combination according to claim 8 wherein the topoisomerase II inhibitor is doxorubicin.

10. The combination according to claim 1 wherein the antimitotic agent is selected from the group consisting of paclitaxel, docetaxel, ixabepilone, vinblastine, vincristine, vindesine and vinorelbine.

11. The combination according to claim 10 wherein the antimitotic agent is paclitaxel.

12. The combination according to claim 1 wherein the kinase inhibitor is selected from the group consisting of sorafenib, dasatinib, gefitinib, erlotinib, sunitinib, imatinib, nilotinib and lapatinib.

13. The combination according to claim 12 wherein the kinase inhibitor is sorafenib or dasatinib.

14. The combination according to claim 1 wherein the proteasome inhibitor is bortezomib.

15. The combination according to claim 1 wherein an antibody inhibiting a growth factor or its receptor is selected from the group consisting of of bevacizumab (antibody to vascular endothelial growth factor), cetuximab, panitumumab, matuzumab, nimotuzumab (antibodies to epidermal growth factor receptor), trastuzumab and pertuzumab (antibodies to ErbB2).

16. The combination according to claim 15 wherein the antibody inhibiting a growth factor or its receptor is bevacizumab.

17. A pharmaceutical composition comprising the combination according to claim 1 in association with a pharmaceutically acceptable carrier, diluent or excipient.

18. The combination according to claim 1 or a pharmaceutical composition comprising the combination according to claim 1 in association with a pharmaceutically acceptable carrier, diluent or excipient, for simultaneous, separate or sequential use.

19. A commercial kit comprising, in a suitable container means, a combination as defined in claim 1 or a pharmaceutical composition comprising the combination according to claim 1 in association with a pharmaceutically acceptable carrier, diluent or excipient, for simultaneous, separate or sequential use thereof.

* * * * *